United States Patent [19]

Harandi et al.

[11] Patent Number: 4,788,366
[45] Date of Patent: Nov. 29, 1988

[54] PRODUCTION OF HEAVIER HYDROCARBONS FROM LIGHT OLEFINS IN MULTISTAGE CATALYTIC REACTORS

[75] Inventors: Mohsen N. Harandi, Lawrenceville; Hartley Owen, Belle Mead; Samuel A. Tabak, Wenonah, all of N.J.

[73] Assignee: Mobil Oil Corporation, New York, N.Y.

[21] Appl. No.: 137,913

[22] Filed: Dec. 28, 1987

[51] Int. Cl.$^4$ .............................................. C07C 2/00
[52] U.S. Cl. ................................. 585/314; 585/301; 585/303; 585/312; 585/315; 585/415
[58] Field of Search ............... 585/301, 303, 312, 314, 585/315, 415

[56] References Cited

U.S. PATENT DOCUMENTS

| | | | |
|---|---|---|---|
| 3,760,024 | 6/1971 | Cattanach | 260/673 |
| 4,433,185 | 2/1984 | Tabak | 585/312 |
| 4,444,988 | 4/1984 | Capsuto et al. | 585/415 |
| 4,450,311 | 5/1984 | Wright et al. | 585/413 |
| 4,456,779 | 6/1984 | Owen et al. | 585/415 |
| 4,482,772 | 11/1983 | Tabak | 585/254 |
| 4,487,985 | 12/1984 | Tabak | 585/517 |
| 4,511,747 | 4/1985 | Wright et al. | 585/415 |
| 4,543,435 | 9/1985 | Gould et al. | 585/330 |
| 4,605,807 | 5/1985 | Mazurek | 585/517 |

Primary Examiner—Asok Pal
Attorney, Agent, or Firm—Alexander J. McKillop; Michael G. Gilman; L. G. Wise

[57] ABSTRACT

A multi-stage catalytic olefin upgrading technique for converting lower olefinic feedstock to heavier liquid hydrocarbon product. The invention provides a fluid bed continuous primary stage reaction zone with shape selective medium pore zeolite oligomerization catalyst particles to convert at least a portion of the lower olefinic components to intermediate olefinic hydrocarbons containing olefinic and aromatic components; cooling primary stage reaction effluent to condense at least a portion of the intermediate hydrocarbons; feeding a second olefinic stream to a serially arranged multi-reactor secondary stage for upgrading lower olefins; quenching partially upgraded secondary stage olefins with primary stage liquid; and further contacting the quenched mixture including aromatics from the primary stage with shape selective medium pore zeolite olgiomerization catalyst in a high pressure fix bed secondary stage distillate mode catalytic reactor at elevated temperature and high prssure to provide a heavier hydrocarbon effluent stream comprising distillate hydrocarbons.

4 Claims, 2 Drawing Sheets

PRODUCTION OF HEAVIER HYDROCARBONS FROM LIGHT OLEFINS IN MULTISTAGE CATALYTIC REACTORS

BACKGROUND OF THE INVENTION

This invention relates to a process and operating system for upgrading light olefins to liquid hydrocarbons. In particular, it provides a continuous process for oligomerizing olefinic feedstock to produce distillate product for use as diesel fuel or the like. It provides a technique for oligomerizing lower alkene-containing light gas feedstock, optionally containing ethene, propene, and/or butylenes, to produce predominantly $C_{10}+$ distillate hydrocarbons and a minor amount of olefinic gasoline and other useful products.

Developments in zeolite catalysis and hydrocarbon conversion processes have created interest in utilizing olefinic feedstocks for producing $C_5+$ gasoline, diesel fuel, distillates, lubricant stocks, etc. In addition to basic chemical reactions promoted by ZSM-5 type zeolite catalysts, a number of discoveries have contributed to the development of new industrial processes. These are safe, environmentally acceptable processes for utilizing feedstocks that contain lower olefins, especially $C_2$–$C_4$ alkenes. Conversion of $C_2$–$C_4$ alkenes and alkanes to produce aromatics-rich liquid hydrocarbon products were found by Cattanach (U.S. Pat. No. 3,760,024) and Yan et al (U.S. Pat. No. 3,845,150) to be effective processes using the ZSM-5 type zeolite catalysts. In U.S. Pat. Nos. 3,960,978 and 4,021,502, Plank, Rosinski and Givens disclose conversion of $C_2$–$C_5$ olefins, alone or in admixture with paraffinic components, into higher hydrocarbons over crystalline zeolites having controlled acidity. Garwood et al. have also contributed to the understanding of catalytic olefin upgrading techniques and improved processes as in U.S. Pat. Nos. 4,150,062, 4,211,640 and 4,227,992. The above-identified disclosures are incorporated herein by reference.

Conversion of lower olefins, especially ethene, propene and butenes, over HZSM-5 is effective at moderately elevated temperatures and pressures. The conversion products are sought as liquid fuels, especially the $C_5+$ hydrocarbons. Product distribution for liquid hydrocarbons can be varied by controlling process conditions, such as temperature, pressure and space velocity. Olefinic gasoline (e.g., $C_5$–$C_9$) is readily formed at elevated temperature (e.g., up to about 350° C.) and moderate pressure from ambient to about 5500 kPa, preferably about 250 to 2900 kPa. Under appropriate conditions of catalyst activity, reaction temperature and space velocity, predominantly olefinic gasoline can be produced in good yield and may be recovered as a product or fed to a high pressure reactor system containing high acid acitivity catalyst for further conversion to heavier hydrocarbons, especially $C_{10}$–$C_{20}$ distillate-range products. Distillate mode operation can be employed to maximize production of $C_{10}+$ aliphatics by reacting the lower and intermediate olefins at high pressure and moderate temperature. Operating details for typical olefin oligomerization units are disclosed in U.S. Pat. Nos. 4,456,779; 4,497,968 (Owen et al.) and 4,433,185 (Tabak), incorporated herein by reference. At moderate temperature and relatively high pressure, the conversion conditions favor production of distillate-range product having a normal boiling point of at least 165° C. (330° F.). Lubricants can be manufactured by multistage reactors according to U.S. Pat. Nos. 4,520,215 and 4,568,786 (Chen and Tabak). Lower olefinic feedstocks containing $C_2$–$C_4$ alkenes may be converted selectively. While propene and butene may be converted to the extent of 50% to 99% at moderate temperature, only about 10% to 30% of ethene will be converted using only HZSM-5 or similar process conditions and acid zeolites.

It has been found that olefinic light gas rich in $C_2$–$C_4$ alkene can be upgraded to intermediate dimer and trimer liquid hydrocarbons rich in heavier $C_6$–$C_{12}$ olefinic hydrocarbons by catalytic conversion in a fixed bed or turbulent fluidized bed of solid acid zeolite catalyst at a high space velocity and under controlled reaction severity conditions to prevent substantial formation of aromatics. This technique is particularly useful in a two-stage process for upgrading olefinic components of LPG and FCC light gas. Typical feedstock may contain significant amounts of ethene, propene, butenes, $C_2$–$C_4$ paraffins and hydrogen produced in cracking heavy petroleum oils or the like. It is a primary object of the present invention to provide a novel technique for upgrading such lower olefinic feedstock to heavier lubricants, distillate and gasoline range hydrocarbons in an economic multistage reactor system.

SUMMARY OF THE INVENTION

An improved multistage catalytic process has been found for conversion of light olefinic gas feedstock, especially olefinic $C_2$–$C_4$ hydrocarbons, to distillate range hydrocarbons rich in $C_{10}+$ aliphatics and alkylated aromatics, comprising the methods and means for:

(a) maintaining a fluidized bed of medium pore acid zeolite catalyst particles in a primary reaction stage in a turbulent reactor bed maintained under reaction severity conditions effective to convert a primary ethene-containing olefinic feedstream by passing hot feedstock vapor upwardly through the fluidized catalyst bed at reaction severity conditions sufficient to convert olefins substantially to intermediate range olefins and aromatics in the $C_5$–$C_9$ range;

(b) recovering primary stage effluent, including a liquid stream containing a major amount of $C_5+$ hydrocarbons;

(c) contacting a secondary olefinic feedstream comprising $C_3$–$C_4$ olefins in a secondary catalytic reactor stage with a series of fixed catalyst bed reactors containing medium pore acid zeolite oligomerizaiton catalyst at high pressure under distillate mode oligomerization conditions;

(d) mixing at least a portion of liquid primary stage effluent containing aromatic hydrocarbons with at least one hot inter-reactor stream containing partially upgraded olefins in the secondary stage, thereby quenching said inter-reactor stream; and (e) coreacting said mixed stream containing partially upgraded olefins and intermediate primary stage hydrocarbons in at least one secondary stage reactor to provide distillate range hydrocarbon product.

THE DRAWINGS

FIG. 1 is a process flow diagram depicting the overall process unit operations; and FIG. 2 is a schematic view of a fluidized bed reactor system according to the present invention.

DESCRIPTION OF PREFERRED EMBODIMENTS

In this description, metric units and parts by weight are employed unless otherwise stated.

In the discussion of the inventive process, the various feedstock materials may be designated as primary and secondary streams, not with regard to their importance or proportions, but to distinguish between their compositions and conversion characteristics for their respective reactor stages. Both primary and secondary feedstocks may contain a mixture of lower olefins, such as present in crackate gas derived by catalytic cracking of petroleum fractions.

The primary feedstock stream contains a significant amount of ethene (ethylene); whereas this component may be present in only minor amounts in the secondary feedstock stream. A typical primary feestream is FCC fuel gas, usually rich in ethene, ethane, methane, hydrogen; and lean in $C_{3+}$ hydrocarbon components.

The preferred secondary feedstock contains $C_{3+}$ alkenes, such as mono-olefinic propene and butenes, wherein the total $C_3$-$C_6$ alkenes are in the range of about 10 to 80 wt %. Non-deleterious components, such as paraffins and inert gases, may be present. A particularly useful secondary feedstock is LPG light gas byproduct of FCC gas oil cracking units containing typically 20-60 mol % $C_3$-$C_4$ olefins. The process may be tolerant of a wide range of lower alkanes, from 0 to 95%. Preferred feedstocks contain more than 50 wt. % $C_3$-$C_4$ lower aliphatic hydrocarbons, and contain sufficient olefins to provide total olefinic partial pressure of at least 1400 kPa.

The primary reactor is advantageously configured as a fludized catalyst bed. The main advantages of the fluid bed configurations are its flexibility for running various feedstock and temperature control.

Multistage System Operation

Figure 1:
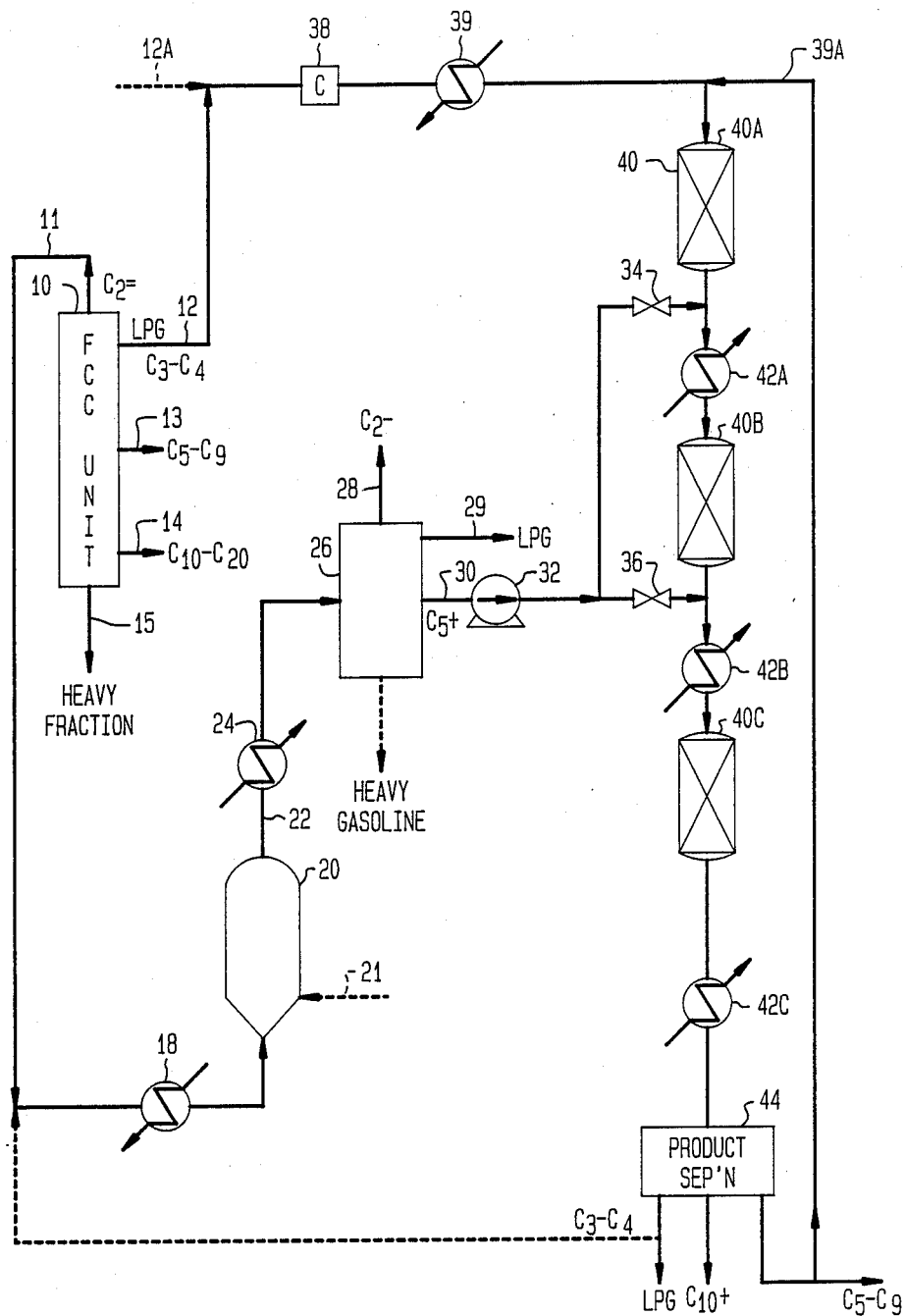

In FIG. 1 a typical multistage olefins upgrading system is depicted by a schematic process diagram. A fluid catalytic cracking (FCC) unit 10 is provided with means for fractionating FCC effluent into an ethene-containing $C_2$− light gas stream 11, a second LPG gas stream 12 rich in propene and butenes, a light olefinic naphtha stream 13 rich in $C_5$-$C_9$ aliphatics, a distillate stream 14, and a heavy hydrocarbon fraction 15. The primary olefinic feedstock is introduced via inlet conduit 11 and heat exchanger 18 to the bottom inlet of primary stage reactor means 20. Additional feedstock or recycle may be injected optionally via line 21. A preferred reactor design is shown in detail in FIG. 2. Hot effluent gas passes via conduit 22 to condenser cooler means 24, wherein a major portion of the $C_5$-$C_9$ light gasoline hydrocarbons are condensed and separated in primary separation unit 26 to provide one or more light gas streams 28, 29 rich in unreacted $C_4$− aliphatics, and a condensed liquid stream 30 containing a large amount of olefinic intermediate components and about 1 to 20 wt % of aromatic components. Fluid handling means is operatively connected between stages to receive, store and pump liquid hydrocarbons within the system. The condensed liquid hydrocarbons are withdrawn from storage and/or taken directly from upstream processing units via pump means 32 and passed through valve means 34, 36 to the secondary stage for inter-reactor quenching.

The secondary reaction stage feedstream 12 contains predominantly $C_3$-$C_4$ aliphatics, optionally supplemented by stream 12A, and is passed via compressor means 38 and heat exchange means 39 to the inlet of the secondary stage reaction section 40. Typically the secondary feedstream is pressurized to about 2800 to 10,000 kPa and heated to about 235° C.-315° C., along with any recycle or diluent stream, e.g. 39A. Secondary reaction zone 40 may be configured as adiabatic fixed bed reactors, especially as a plurality of serially connected beds 40A, 40B, 40C with inter-reactor cooling means 42A, 42B, as described in U.S. Pat. No. 4,456,779 (Owen et al), incorporated by reference. This prior patent also gives details of equipment and regeneration operation for oxidative regeneration of a typical fixed bed reactor system.

The hot effluent streams from at least one of the front beds 40A, 40B may be quenched by cold liquid intermediate streams from the primary stage separation means 26 via valves 34 and /or 36. The aromatic components of the primary stage intermediate fraction are further reacted by catalystic alkylation by olefinic components derived from the secondary stage upgrading reactions. These hydrocarbons are further upgraded to distillate range hydrocarbon product in contact with at least one downstream bed of oligomerization catalyst. The secondary stage reaction zone is maintained in distillate operating mode at moderately elevated temperature and high pressure favorable to formation of $C_{10+}$ aliphatic product. The secondary stage effluent stream is cooled by exchanger 42C and passed to product separation and recovery means 44. A liquid stream rich in $C_5$-$C_9$ hydrocarbons may be pressurized and recycled via line 39A for mixture with fresh secondary olefinic feed from the primary stage or recovered as gasoline product.

The present system is flexible with regard to composition of feedstock and conversion. Advantageously, the gaseous primary effluent components are separated from the $C_{5+}$ rich liquid stream in a phase separator unit 26 or the like. Light gas stream 28, containing $C_2$ and lighter gaseous components may be removed from the system as off gas for fuel, or part of it may be recycled via line 11 or 21 to the primary stage reactor 20. Although it is often most advantageous and economic to operate the primary stage reactor as a single pass unit, recycle of unreacted $C_4$− may be considered as an optional processing technique. It is possible to generate olefins in situ by feeding methanol or other olefin precursors to the primary stage reactor. In addition, first stage LPG product can optionally be upgraded in the second stage reaction system. Other interstage processing equipment and operating steps are fully described in U.S. Pat. No. 4,497,968 (Wright et al).

Description of Catalysts

Recent developments in zeolite technology have provided a group of medium pore siliceous materials having similar pore geometry. Most prominent among these intermediate pore size zeolites is ZSM-5, which is usually synthesized with Bronsted acid active sites by incorporating a tetrahedrally coordinated metal, such as Al, Ga, B or Fe, within the zeolitic framework. These medium pore zeolites are favored for acid catalysis; however, the advantages of ZSM-5 structures may be utilized by employing highly siliceous materials or cystalline metallosilicate having one or more tetrahedral species having varying degrees of acidity. ZSM-5 crystalline structure is readily recognized by its X-ray diffraction pattern, which is described in U.S. Pat. No. 3,702,866 (Argauer, et al.), incorporated by reference.

The oligomerization catalysts preferred for use herein include the medium pore (i.e., about 5-7A) shape-selective crystalline aluminosilicate zeolites having a silica-to-alumina ratio of at least 12, a constraint index of about 1 to 12 and significant Bronsted acid activity. In the primary stage reactor the coked catalyst preferably have an acid activity (alpha value) of about 0.1 to 20 under steady state process conditions to achieve the required degree of reaction severity. The second stage catalyst is generally more active (e.g.—alpha value of 10–200 or higher). Representative of the ZSM-5 type zeolites are ZSM-5, ZSM-11, ZSM-12, ZSM-22, ZSM-23, and ZSM-35. ZSM-5 is disclosed in U.S. Pat. No. 3,702,886 and U.S. Pat. No. Re. 29,948. Other suitable zeolites are disclosed in U.S. Pat. Nos. 3,709,979; 3,832,449; 4,076,979; 3,832,449; 4,076,842; 4,016,245 and 4,046,839; 4,414,423; 4,417,086; 4,517,396 and 4,542,251. The disclosures of these patents are incorporated herein by reference. While suitable zeolites having a coordinated metal oxide to silica molar ratio of 20:1 to 200:1 or higher may be used, it is advantageous to employ a standard ZSM-5 having a silica alumina molar ratio of about 25:1 to 70:1, suitably modified. A typical zeolite catalyst component having Bronsted acid sites may consist essentially of crystalline aluminosilicate having the structure of ZSM-5 zeolite with 5 to 95 wt. % silica, clay and/or alumina binder.

These siliceous zeolites may be employed in their acid form, ion exchanged or impregnated with one or more suitable metals, such as Ga, Pd, Zn, Ni, Co and/or other metals of Periodic Groups III to VIII. Gallium and other metals are known to promote aromatics formation under the process conditions of the primary stage reactor. Ni-exchanged or impregnated catalyst is particularly useful in converting ethene under low severity conditions. The zeolite may include other components, generally one or more metals of group IB, IIB, IIIB, VA, VIA or VIIIA of the Periodic Table (IUPAC). Useful hydrogenation components include the noble metals of Group VIIIA, especially platinum, but other noble metals, such as palladium, gold, silver, rhenium or rhodium, may also be used. Base metal hydrogenation components may also be used, especially nickel, cobalt, molybdenum, tungsten, copper or zinc. The catalyst materials may include two or more catalytic components, such as a metallic oligomerization component (e.g., ionic $Ni^{+2}$, and a shape-selective medium pore acidic oligomerization catalyst, such as ZSM-5 zeolite) which components may be present in admixture or combined in a unitary bifunctional solid particle. It is possible to utilize an ethene dimerization metal or oligomerization agent to effectively convert feedstock ethene in a continuous reaction zone. Certain of the ZSM-5 type medium pore shape selective catalysts are sometimes known as pentasils. In addition to the preferred aluminosilicates, the borosilicate, ferrosilicate and "silicalite" materials may be employed.

ZSM-5 type pentasil zeolites are particularly useful in the process because of their regenerability, long life and stability under the extreme conditions of operation. Usually the zeolite crystals have a crystal size from about 0.01 to over 2 microns or more, with 0.02-1 micron being preferred.

Catalyst versatility permits similar zeolites to be used in both the primary stage and distillate mode secondary oligomerization stage. While it is within the inventive concept to employ substantially different catalysts in these stages, it is advantageous to employ a standard ZSM-5, suitability modified. In the description of preferred embodiments primary stage fluidized bed catalyst particles consist essentially of 25% H-ZSM-5 catalyst contained within a silica-alumina matrix and having a fresh alpha value of less than about 100, based on total catalyst weight. The secondary stage catalyst may consist of a standard 70:1 aluminosilicate H-ZSM-5 extrudate having an acid value of at least 20, preferably 150 or higher.

Stage I—Primary Stage Operation

The preferred primary stage reactor is a fluidized reactor system operating under turbulent fluidization. Particle size distribution can be a significant factor in achieving overall homogeneity in turbulent regime fluidization. It is desired to operate the process with particles that will mix well throughout the bed. Large particles having a particle size greater than 250 microns should be avoided, and it is advantageous to employ a particle size range consisting essentially of 1 to 150 microns. Average particle size is usually about 20 to 100 microns, preferably 40 to 80 microns. Particle distribution may be enhanced by having a mixture of larger and smaller particles within the operative range, and it is particularly desirable to have a significant amount of fines. Close control of distribution can be maintained to keep about 10 to 25 wt % of the total catalyst in the reaction zone in the size range less than 32 microns. This class of fluidizable particles is classified as Geldart Group A. Accordingly, the fluidization regime is controlled to assure operation between the transition velocity and transport velocity. Fluidization conditions are substantially different from those found in non-turbulent dense beds or transport beds.

The primary stage products are mainly $C_5$ to $C_9$ hydrocarbons, which will comprise at least 50 wt. % of the recovered product, preferrably 80% or more. Depending upon the reaction conditions, this intermediate stream may comprise olefins as the predominant fraction of the $C_5+$ reaction effluent, up to 90% pentenes, hexenes, heptenes, octenes, nonenes and heavier olefins. However, it is feasible to coproduce with these olefinic intermediates a $C_6+$ aromatic gasoline component by increasing reaction temperature and severity to effect cyclization. Aromatics production can be increased by known operating techniques. The reaction severity conditions can be controlled to optimize yield of benzene, toluene, xylenes (BTX) aromatics or $C_5+$ aliphatic hydrocarbons. It is understood that aromatics and light paraffin production is promoted by those zeolite catalysts having a high concentration of Bronsted acid reaction sites. Accordingly, an important criterion is selecting and maintaining catalyst inventory to provide either fresh catalyst having acid activity or by controlling primary stage catalyst deactivation and regeneration rates to provide an average acid cracking activity (alpha value) of about 1 to 100, preferably about 3–20, based on total catalyst solids.

Reaction temperatures and contact time are also significant factors in determining the reaction severity, and the process parameters are followed to give a substantially steady state condition wherein the reaction severity is maintained within the limits which yield a desired weight ratio of alkane to alkene produced in the reaction zone.

This technique is particularly useful for operation with a fluidized catalytic cracking (FCC) unit to increase overall production of liquid product in fuel gas limited petroleum refineries. Light olefins and some of the light paraffins, such as those in FCC light gas, can be converted to valuable $C_5+$ gasoline and $C_{10}+$ distillate hydrocarbon products in a multistage reactor containing a zeolite catalyst. In addition to $C_2-C_4$ olefin upgrading, the load to the refinery fuel gas plant is decreased considerably.

Figure 2:
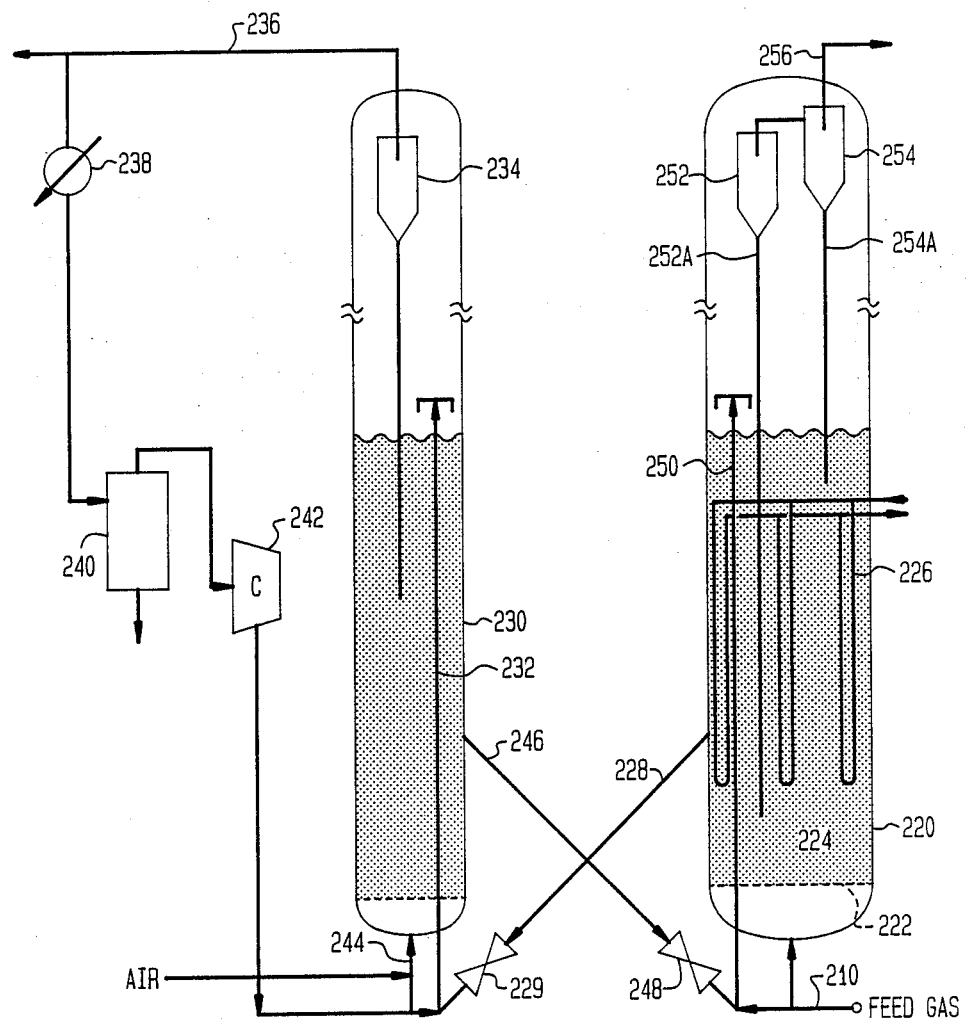

Referring now to FIG. 2, the primary stage feed gas rich in lower olefins passes under pressure through conduit 210, with the main flow being directed through the bottom inlet of reactor vessel 220 for distribution through grid plate 222 into the fluidization zone 224. Here the feed gas contacts the turbulent bed of finely divided catalyst particles. Reactor vessel 220 is shown provided with heat exchange tubes 226. The bottoms of the tubes are spaced above feed distributor grid 222 sufficiently to be free of jet action by the charged feed through the small diameter holes in the grid. Advantageously, no internal cooling coils are required whenever reaction heat can be partially or completely removed by using cold feed. Baffles may be added to control radial and axial mixing. Although depicted without baffles, the vertical reaction zone can contain open end tubes above the grid for maintaining hydraulic constraints, as disclosed in U.S. Pat. No. 4,251,484 (Daviduk and Haddad). Heat released from the reaction can be controlled by adjusting feed temperature in a known manner.

Catalyst outlet means 228 is provided for withdrawing catalyst from above bed 224 and passed for catalyst regeneration in vessel 230 via control valve 229. The partially deactivated catalyst is oxidatively regenerated by controlled contact with air or other regeneration gas at elevated temperature in a fluidized regeneration zone to remove carbonaceous deposits and restore acid acitivity. The catalyst particles are entrained in a lift gas and transported via riser tube 232 to a top portion of vessel 230. Air is distributed at the bottom of the bed to effect fluidization, with oxidation byproducts being carried out of the regeneration zone through cyclone separator 234, which returns any entrained solids to the bed. Flue gas is withdrawn via top conduit 236 for disposal; however, a portion of the flue gas may be recirculated via heat exchanger 238, separator 240, and compressor 242 for return to the vessel with fresh oxidation gas via line 244 and as lift gas for the catalyst in riser 232.

Regenerated catalyst is passed to the main reactor 220 through conduit 46 provided with flow control valve 248. The regenerated catalyst may be lifted to the catalyst bed with pressurized feed gas through catalyst return riser conduit 50. Since the amount of regenerated catalyst passed to the reactor is relatively small, the temperature of the regenerated catalyst does not upset the temperature constraints of the reactor operations in significant amount. A series of sequentially connected cyclone separators 252, 254 are provided with diplegs 252A, 254A to return any entrained catalyst fines to the lower bed. These separators are positioned in an upper portion of the reactor vessel comprising dispersed catalyst phase 224. Advantageously, filters, such as sintered metal plate filters, can be used alone or conjunction with cyclones.

The product effluent separated from catalyst particles in the cyclone separating system is then withdrawn from the reactor vessel 220 through top gas outlet means 256.

The recovered hydrocarbon product comprising $C_5+$ olefins and/or aromatics, paraffins and naphthenes is thereafter processed as required to provide a desired gasoline and/or higher boiling product.

Under optimized process conditions the turbulent bed may have a superficial vapor velocity of about 0.2 to 2 meters per second (m/sec). The velocity specified here is for an operation at a total reactor pressure of about 100 to 300 kPa. Those skilled in the art will appreciate that at higher pressures, a lower gas velocity may be employed to ensure operation in the turbulent fluidization regime. A convenient measure of turbulent fluidization is the bed density. A typical turbulent bed has an operating density of about 100 to 500 kg/m$^3$, preferably about 300 to 500 kg/m$^3$, measured at the bottom of the reaction zone, becoming less dense toward the top of the reaction zone, due to pressure drop and particle size differentiation. The weight hourly space velocity and uniform contact provides a close control of contact time between vapor and solid phases. The weight hourly space velocity (WHSV, based on total olefins in the fresh feedstock) is usually about 0.1 to 10 WHSV. The fluidized bed unit can be operated over a wide range of process variables and catalyst activity.

Fluidized Bed Reactor Operation

A typical reactor unit employs a temperature-controlled catalyst zone with indirect heat exchange and/or adjustable gas preheat, whereby the reaction exotherm can be carefully controlled to prevent excessive temperature above the usual operating range of about 260° C. to 650° C. To promote olefin production, preferably an average reactor temperature of 300° C. to 400° C. is maintained. However, aromatics production is favored by higher temperature, e.g.—500° C.–650° C. Energy conservation in the system may utilize at least a portion of the reactor exotherm heat value by exchanging hot reactor effluent with feedstock and/or recycle streams. Optional heat exchangers may recover heat from the effluent stream prior to fractionation. The use of a fluid-bed reactor in the primary stage offers several advantages over a fixed-bed reactor. Due to continuous catalyst regeneration, fluid-bed reactor operation will not be adversely affected by oxygenate, sulfur and/or nitrogen containing contaminants presented in the feed gas.

Stage II—Distillate Mode Oligomerization Reactor Operation

The secondary distillate prodution stage provides catalytic oligomerization reactor means, preferrably a fixed bed system containing medium pore shape selective acid zeolite oligomerization catalyst for converting fresh $C_3-C_4$ rich feed and intermediate range hydrocarbons from Stage I to liquid hydrocarbons comprising a major amount of distillate. The secondary feed stream is preheated by indirect heat exchange with a hot stream, such as, distillate product or first stage reactor effluent, in exchanger 39 and passed to the Stage II reactor 40 at a pressure of at least about 2800 kPa, preferably about 4225 to 7000 kPa (600 to 1000 psig) for light distillate production and higher pressure (e.g. 10,000 kPa) for heavy distillate or lube production. In FIG. 1 a single train distillate mode fixed bed secondary stage reactor system is depicted. Depending upon the effluent temperature and relative flow rates of the primary stage $C_5+$ liquid and partially converted secondary reactor effluent the plural reactor system may be employed with liquid quenching alone or with additional inter-reactor cooling, whereby the reaction exotherm can be carefully controlled to optimize the normal moderate temperature window of about 190° C. to 315° C. (375°–600° F.) and a total pressure of 4225 kPa (600 psig), with a minimum olefin partial pressure at the inlet of about 1100 kPa (160 psig). Advantageously, the space velocity (WHSV based on fresh olefin feed) is about 0.1 to 1.5. Preferably, the secondary stage reactor conditions are optimized to produce heavy liquid hydrocarbons having a normal boiling above 165° C. (330° F.). Product fractionation is achieved by typical product fractionation systems as described in U.S. Pat. Nos. 4,456,779 and 4,504,693 (Owen et al).

It is within the inventive concept to cascade a major amount of $C_5+$ hydrocarbons, including intermediate olefins, light BTX aromatics and heavy gasoline directly from the primary stage into the distillate mode reactor. This will optimize the continuous process and will maximize distillate production by alkylating aromatics and upgrading olefinic gasoline boiling range components.

For purposes of comparing the improved integrated process with single process unit operations two FCC feedstreams are converted independently in a distillate mode fixed bed oligomerization reactor system and a fluid bed olefins to gasoline reactor system. Feed No. 1 is mainly $C_3$-$C_4$ olefins from LPG crackate, and Feed No. 2 is an ethene-containing FCC light gas (normally used as fuel gas). Table 1 summarizes the feed compositions and products from each independent unit operation, and further demonstrates the improved yield of $C_{11}+$ distillate product by the integrated process of this invention, wherein $C_5+$ gasoline from the fluid bed reactor product is introduced between fixed bed reactors in the distillate mode reactor system. The thru material balances are based on equivalent parts of feed, expressed as parts by weight.

maintaining a fluidized bed of medium pore acid zeolite catalyst particles in a primary reaction stage in a turbulent reactor bed maintained under reaction severity conditions effective to convert a primary ethene-containing olefinic feedstream by passing hot feedstock vapor upwardly through the fluidized catalyst bed at reaction severity conditions sufficient to convert ethene substantially to intermediate range olefins and aromatics in the $C_5$-$C_9$ range;

recovering primary stage effluent, including a liquid stream containing a major amount of aromatics-rich $C_5+$ hydrocarbons;

contacting a secondary olefinic feedstream comprising $C_3$-$C_4$ olefins in a secondary catalytic reactor stage with a series of fixed catalyst bed reactors containing shape selective medium pore acid zeolite oligomerization catalyst at high pressure under distillate mode oligomerization conditions;

mixing at least a portion of liquid primary stage effluent containing aromatic hydrocarbons with at least one hot inter-reactor stream containing partially upgraded olefins in the secondary stage, thereby quenching said inter-reactor stream; and coreacting said mixed stream containing partially upgraded olefins and intermediate primary stage hydrocarbons in at least one secondary stage reactor to provide distillate range hydrocarbon product.

2. The process of claim 1 wherein the primary and secondary stage catalyst comprises a siliceous metallosilicate acid zeolite having the structure of ZSM-5 zeolite.

3. The process of claim 1 wherein the secondary stage feedstream consists essentially of $C_2$-$C_4$ light cracking gas comprising about 10 to 80 wt % total propane and butenes, and wherein the primary stage effluent contains about 10 to 25 wt % aromatics.

4. The process of claim 1 wherein the secondary olefinic feedstream contains predominantly $C_3$-$C_4$ ali-

TABLE 1

| | CONVERSION OF FCC OLEFINS TO GASOLINE & DISTILLATE (BASED ON WEIGHT LPG FEED) | | | | | |
|---|---|---|---|---|---|---|
| | DISTILLATE MODE | | GASOLINE MODE | | | |
| | FEED | PRODUCT | FEED | PRODUCT | INTEGRATED PROCESS | |
| No. 3 | No. 1 | No. 1 | No. 2 | No. 2 | TOTAL FEED | PRODUCT |
| $C_2-$ & Inerts | — | — | 24.1 | 24.9 | 24.1 | 24.9 |
| $C_2=$ | — | — | 7.9 | 1.6 | 7.9 | 1.6 |
| $C_3=$ | 25.5 | 0.1 | 9.8 | 1.0 | 35.3 | 0.1 |
| $C_3$ | 7.6 | 8.3 | 3.0 | 3.6 | 10.6 | 12.6 |
| $C_4=$ | 43.7 | 1.2 | 3.7 | 0.5 | 47.4 | 1.3 |
| $C_4$ | 23.2 | 24.6 | 3.0 | 4.6 | 26.2 | 29.7 |
| $C_5+$ Gasoline | — | 20.6 | 6.3 | 21.6 | 6.3 | 34.7 |
| $C_{11}+$ Distillate | — | 45.2 | — | — | — | 52.9 |
| Total | 100 | 100 | 57.8 | 57.8 | 157.8 | 157.8 |

While the invention has been shown by describing preferred embodiments of the process, there is no intent to limit the inventive concept, except as set forth in the following claims.

We claim:

1. A continuous multistage catlytic process for conversion of light olefins to distillate range hydrocarbons rich in $C_{10}+$ aliphatics, comprising the steps of:

phatic hyddrocarbons; said secondary reactor stage is maintained at pressure of 2800 to 10,000 kPa and temperatue of 235° C.–315° C.; and wherein aromatic components of the primary stage liquid effluent stream are further reacted by catalytic alkylation by olefinic components to provide distillate range hydrocarbon product.

* * * * *